(12) United States Patent
Noh et al.

(10) Patent No.: US 9,823,229 B2
(45) Date of Patent: Nov. 21, 2017

(54) HYDROGEN SENSOR AND METHOD FOR MANUFACTURING THE SAME

(71) Applicants: Hyundai Motor Company, Seoul (KR); Ajou University Industry-Academic Cooperation Foundation, Suwon, Gyeonggi-do (KR)

(72) Inventors: Yong Gyu Noh, Gyeonggi-do (KR); Se Kwon Jung, Seoul (KR); Chi Myung Kim, Gyeonggi-do (KR); Hyung Tak Seo, Seoul (KR); Yeong An Lee, Gyeongsangnam-do (KR)

(73) Assignees: Hyundai Motor Company, Seoul (KR); Ajou University Industry-Academic Cooperation Foundation, Suwon, Gyeonggi-Do (KR)

( * ) Notice: Subject to any disclaimer, the term of this patent is extended or adjusted under 35 U.S.C. 154(b) by 92 days.

(21) Appl. No.: 14/569,727

(22) Filed: Dec. 14, 2014

(65) Prior Publication Data

US 2016/0054277 A1 Feb. 25, 2016

(30) Foreign Application Priority Data

Aug. 21, 2014 (KR) ........................ 10-2014-0109121

(51) Int. Cl.
*G01N 15/06* (2006.01)
*G01N 33/00* (2006.01)
*G01N 33/48* (2006.01)
*G01N 31/10* (2006.01)

(52) U.S. Cl.
CPC ................... *G01N 31/10* (2013.01)

(58) Field of Classification Search
CPC ........ G01N 15/06; G01N 33/00; G01N 33/48; G01N 21/75; G01N 31/10
USPC ............................................. 422/83, 98, 429
See application file for complete search history.

(56) References Cited

U.S. PATENT DOCUMENTS

| 4,030,340 | A | * | 6/1977 | Chang ......................... 73/31.01 |
| 4,134,818 | A | * | 1/1979 | Pebler et al. ................. 204/406 |
| 5,841,021 | A | * | 11/1998 | De Castro et al. ............ 73/23.2 |
| 2003/0056570 | A1 | * | 3/2003 | Shin et al. .................... 73/25.05 |
| 2011/0209527 | A1 | * | 9/2011 | Miura ........................... 73/25.05 |
| 2011/0259083 | A1 | * | 10/2011 | Lee et al. ..................... 73/31.05 |
| 2013/0255358 | A1 | | 10/2013 | Lee et al. |

FOREIGN PATENT DOCUMENTS

| JP | 2005-233740 A | 9/2005 |
| JP | 2005-345338 A | 12/2005 |
| JP | 3170398 U | 9/2011 |

(Continued)

OTHER PUBLICATIONS

Q. Ashton Action, PhD (ed.), Advances in Nanotechnology Research and Application: 2013 Edition, Scholarly Editions (Jun. 21, 2013) Chapter 1, p. 311.

*Primary Examiner* — Brian J Sines
(74) *Attorney, Agent, or Firm* — Mintz Levin Cohn Ferris Glovsky and Popeo, P.C.; Peter F. Corless

(57) ABSTRACT

A hydrogen sensor and a method for manufacturing the same are provided. The hydrogen sensor includes a metal oxide layer formed over a substrate, and a catalytic pattern that is formed over the metal oxide layer. Further, a protective layer is formed over the catalytic pattern.

5 Claims, 10 Drawing Sheets

(56) References Cited

FOREIGN PATENT DOCUMENTS

| KR | 2006-0111295 A | 10/2006 |
| KR | 2009-0011621 A | 2/2009 |
| KR | 2009-0123042 A | 12/2009 |
| KR | 2013-0106032 A | 9/2013 |

\* cited by examiner

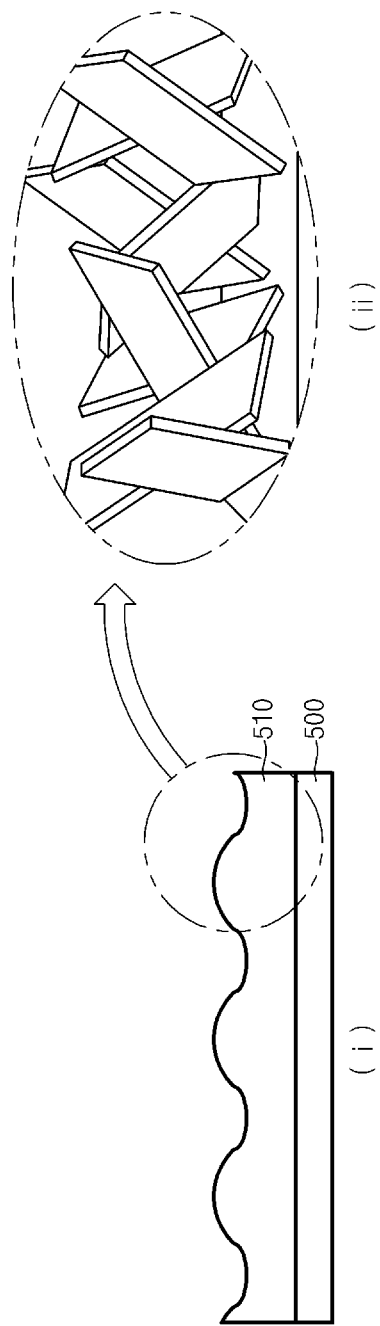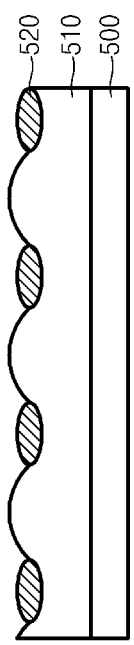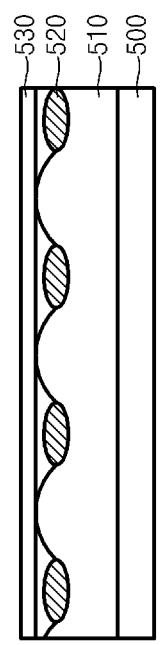
Fig. 10A
Fig. 10B
Fig. 10C

HYDROGEN SENSOR AND METHOD FOR MANUFACTURING THE SAME

CROSS-REFERENCE TO RELATED APPLICATION

The priority of Korean patent application No. 10-2014-0109121 filed on Aug. 21, 2014, the disclosure of which is hereby incorporated in its entirety by reference.

BACKGROUND

Technical Field

The present invention relates to a hydrogen sensor and a method for manufacturing the same, and more particularly to a hydrogen sensor capable of allowing a user to recognize a hydrogen leak (e.g., without extra eyewear).

Description of the Related Art

Hydrogen energy has been considered as a growing alternative to fossil fuels due to an increasing interest in low-pollution alternative energy and environmental pollution from and the exhaustion of fossil fuels. Hydrogen fuels (specifically, commercialization of hydrogen fuel vehicles) may be utilized within the next few years, consumption extension (e.g., increasing the amount of time the hydrogen may be used for) may be desirable in various technical fields such as distributed generation power fields Hydrogen fuel may have unique characteristics (e.g., spontaneous combustion and explosiveness), so safety measures in fabrication and transportation processes of the hydrogen fuel may be necessary. To safely use hydrogen fuel, the critical function of a hydrogen sensor may be to measure hydrogen density and detect a hydrogen leak.

A hydrogen sensor fabricated on the basis of the above requirements includes a catalytic layer, a metal oxide layer, and a sensor protective layer that has sensing selectivity. Hydrogen molecules leaked to the outside pass through the protective layer, and are broken down within the catalytic layer, so that the physical properties of the hydrogen molecules are changed in the metal oxide layer. A movement path of hydrogen gas atoms requires a porous structure, and the hydrogen sensor may need a complicated three-dimensional (3D) path, so the movement speed and the amount of gas may be limited. In addition, a substantially slow movement speed may lead to a substantially slow reaction speed, a smaller amount of gas moved, a less sensitive the sensor, which results in reduction of color variation. In addition, discoloration reflexibility of the metal oxide layer discolored by thickness of a catalytic layer may be decreased.

SUMMARY

The present invention provides a hydrogen sensor and a method for manufacturing the hydrogen sensor. The hydrogen sensor may include a patterned catalytic layer configured to minimize consumption of the catalytic layer, and maximize reaction of hydrogen gas, so discoloration of a metal oxide layer may be recognized.

In accordance with an exemplary embodiment, a hydrogen sensor may include: a metal oxide layer formed over a substrate; a catalytic pattern formed over the metal oxide layer; and a protective layer formed over the catalytic pattern. The hydrogen sensor may further include: at least one first recess formed at an upper portion of the metal oxide layer among the catalytic patterns. Further, the hydrogen sensor may include: a second recess formed over the metal oxide layer, wherein the catalytic pattern is disposed within the second recess.

A top surface of the metal oxide layer may be formed in a substantially embossed shape. The catalytic pattern may be disposed at a lower portion of the embossed metal oxide layers. The metal oxide layer may include one selected from the group consisting of: vanadium (V), niobium (Nb), tantalum (Ta), chromium (Cr), molybdenum (Mo), or tungsten (W). The catalytic pattern may include at least one selected from the group consisting of: palladium (Pd), iridium (Ir), ruthenium (Ru), platinum (Pt), rhodium (Rh), gold (Au), and silver (Ag), or a combination thereof.

In accordance with another exemplary embodiment, a method for manufacturing a hydrogen sensor may include: forming a metal oxide layer over a substrate; forming a catalytic pattern over the metal oxide layer; and forming a protective layer over the catalytic pattern. The formation of the protective layer over the catalytic pattern may include: forming at least one first recess at an upper portion of the metal oxide layer among the catalytic patterns. Further, the formation of the metal oxide layer may include: forming a second recess at a top surface of the metal oxide layer, wherein the top surface of the metal oxide layer may be formed in a substantially embossed shape.

The method may further include: forming the catalytic pattern at a lower portion of the embossed metal oxide layers; and forming the catalytic pattern within the second recess. The metal oxide layer may include one selected from the group consisting of: vanadium (V), niobium (Nb), tantalum (Ta), chromium (Cr), molybdenum (Mo), and tungsten (W). The catalytic pattern may include at least one selected from the group consisting of palladium (Pd), iridium (Ir), ruthenium (Ru), platinum (Pt), rhodium (Rh), gold (Au), and silver (Ag), or a combination thereof.

In accordance with another exemplary embodiment, a hydrogen sensor may include: a metal oxide layer formed over a substrate; a catalytic pattern formed over a substrate disposed between metal oxide patterns; and a protective layer formed over the metal oxide pattern and the catalytic pattern. The catalytic pattern may be formed at a bottom of the metal oxide patterns or may be formed along a sidewall and bottom of the metal oxide patterns. The hydrogen sensor may further include: at least one first recess formed at an upper portion of the catalytic pattern. The metal oxide layer may include at least one selected from the group consisting of: vanadium (V), niobium (Nb), tantalum (Ta), chromium (Cr), molybdenum (Mo), and tungsten (W). The catalytic pattern may include at least one selected from the group consisting of: palladium (Pd), iridium (Ir), ruthenium (Ru), platinum (Pt), rhodium (Rh), gold (Au), and silver (Ag), or a combination thereof.

In accordance with another exemplary embodiment, a method for manufacturing a hydrogen sensor may include: forming a metal oxide pattern over a substrate; forming a catalytic pattern over a substrate disposed between the metal oxide patterns; and forming a protective layer formed over the metal oxide pattern and the catalytic pattern. The formation of the catalytic pattern may include: burying a catalytic layer between the metal oxide patterns; and forming a catalytic pattern that has a step difference with the metal oxide pattern by further etching the buried catalytic layer. The formation of the protective layer over the metal oxide pattern and the catalytic pattern may include: forming a first recess between the catalytic patterns due to a step difference between the metal oxide pattern and the catalytic pattern. In addition, the formation of the catalytic pattern may further include: burying a catalytic layer between the metal oxide patterns; and further etching a substantially center part of the buried catalytic layer so the catalytic layer remains along a sidewall and bottom of the metal oxide patterns. The formation of the protective layer over the metal oxide pattern and the catalytic pattern may include: forming a second recess at an upper portion of the catalytic pattern.

The metal oxide layer may be formed of one selected from the group consisting of: vanadium (V), niobium (Nb), tantalum (Ta), chromium (Cr), molybdenum (Mo), and tungsten (W). The catalytic pattern may be formed of at least one selected from the group consisting of: palladium (Pd), iridium (Ir), ruthenium (Ru), platinum (Pt), rhodium (Rh), gold (Au), and silver (Ag), or a combination thereof. As is apparent from the above description, the exemplary embodiments may include a hydrogen sensor that may have a patterned catalytic layer, so that it may have the following effects.

First, according to application of the patterned catalytic layer, after hydrogen molecules are broken down into hydrogen atoms within the catalytic layer, a reaction may occur within a metal oxide material adjacent to the catalytic layer, such that diffusion speed of hydrogen atoms may not decrease.

Second, the application of the patterned catalytic layer may not interrupt physical property variation and discoloration caused by a reaction between the hydrogen atom and the metal oxide material to maintain discoloration reflexibility of the metal oxide material.

Third, the hydrogen sensor may be configured to detect a physical variation when the hydrogen sensor is exposed to hydrogen. When the hydrogen dissipates (e.g., is no longer present), the hydrogen sensor may return to an initial value. In other words, the hydrogen sensor may be applied to a reversible sensor capable of repeatedly detecting a hydrogen leak.

It is to be understood that both the foregoing general description and the following detailed description of the present invention are exemplary and explanatory and are intended to provide further explanation of the invention as claimed.

BRIEF DESCRIPTION OF THE DRAWINGS

The above and other features of the present invention will now be described in detail with reference to certain exemplary embodiments thereof illustrated in the accompanying drawings which are given herein below by way of illustration only, and thus are not limitative of the present invention, and wherein:

FIGS. 10A to 10C are exemplary cross-sectional views illustrating a method for forming the hydrogen sensor according to an exemplary embodiment of the present invention.

DETAILED DESCRIPTION

Figure 1:
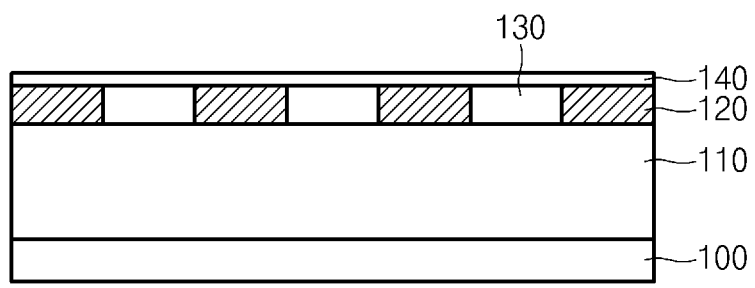
FIG. 1 is an exemplary cross-sectional view illustrating a hydrogen sensor according to an exemplary embodiment of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Reference will now be made in detail to exemplary embodiments of the present invention, examples of which are illustrated in the accompanying drawings. Wherever possible, the same reference numbers will be used throughout the drawings to refer to the same or like parts.

A hydrogen sensor that may be configured to detect hydrogen using the principle that hydrogen gas may be discolored when reacting to a catalyst is provided. The hydrogen sensor may include a metal oxide layer, a catalytic layer, and a protective layer. The catalytic layer may be formed of platinum group metal and may break hydrogen molecules down into hydrogen atoms. The hydrogen atoms broken down by the catalytic layer may be diffused to a metal oxide layer, and may react to the metal oxide material within the metal oxide layer, which may change the physical properties of the hydrogen atoms. The physical properties of the hydrogen atoms may be optically changed within a specific wavelength region, and physical property variation within a visible ray region of about 300 nanometers (nm) to about 800 nm.

Therefore, the hydrogen sensor may use a platinum group noble metal catalytic layer and a transition metal. Further, a hydrogen sensor, formed as a chemochromic thin/thick film or a membrane-type hydrogen sensor, may allow a user to visually recognize a physical property variation. The hydrogen sensor may not require an external power supply and may be warped. In addition, the hydrogen sensor may have superior mounting characteristics, and may be manufactured with substantially low costs.

The exemplary embodiments of present invention relate to a chemochromic hydrogen sensor or a membrane-type hydrogen sensor, and a method for manufacturing the chemochromic hydrogen sensor or the membrane-type hydrogen sensor according to the exemplary embodiments of the present invention will hereinafter be described with reference to the attached drawings.

FIG. 1 is an exemplary cross-sectional view illustrating a hydrogen sensor according to an exemplary embodiment of the present invention. Referring to FIG. 1, the hydrogen sensor may include a substrate 100, a metal oxide layer 110, a catalytic pattern 120, and a protective layer 140. The hydrogen sensor structure will hereinafter be described with reference to FIG. 1. Referring to FIG. 1, a metal oxide layer 110 may be formed over (e.g., on top of) a substrate 100. The substrate 100, disposed at a substantially low (e.g., bottom) part of the hydrogen sensor, may be formed of a flexible plastic or glass material. In addition, the metal oxide layer 110 may be formed of an oxide material that includes one selected from the group consisting of: vanadium (V), niobium (Nb), tantalum (Ta), chromium (Cr), molybdenum (Mo), and tungsten (W).

A plurality of catalytic patterns 120 may be formed over the metal oxide layer 110. The catalytic pattern 120 may break hydrogen molecules down into hydrogen atoms, and may be formed of a platinum group metal that reacts to hydrogen. For example, the platinum group metal may be at least one selected from the group consisting of: palladium (Pd), iridium (Ir), ruthenium (Ru), platinum (Pt), rhodium (Rh), gold (Au), and silver (Ag), or a combination thereof. When hydrogen molecules are broken down into hydrogen atoms within the catalytic layer, the hydrogen atoms may not move toward the metal oxide layer after passing through the catalytic layer, and a reaction may occur within the metal oxide material contiguous to the catalytic layer, to prevent a diffusion speed of the hydrogen atoms.

Physical property variation and discoloration, caused by a reaction between the metal oxide material and the hydrogen atom, may maintain discoloration reflexibility of the metal oxide material. In addition, the patterned catalytic layer may detect physical variation when the hydrogen sensor is exposed to hydrogen. Further, the hydrogen sensor may return to an initial value (e.g., starting value) when hydrogen dissipates (e.g., is no longer detected).

A first recess 130 may be formed at an upper (e.g., top) portion of the metal oxide layer 110 between the catalytic patterns 120. The protective layer 140 may be formed over the catalytic pattern 120 and the first recess 130. In particular, the received hydrogen molecules or hydrogen atoms may remain within the first recess 130, which results in an increase in activity of the catalytic pattern 120 that causes the reaction. The first recess 130 may be in a vacuum state. When hydrogen gas is received, the first recess 130 may contain hydrogen and air. The protective layer 140 may prevent external (e.g., outside) moisture or undesired gas from being applied to the hydrogen sensor. The protective layer 140 may improve durability by protecting the hydrogen sensor, and may also improve gas selectivity.

Figure 2A:
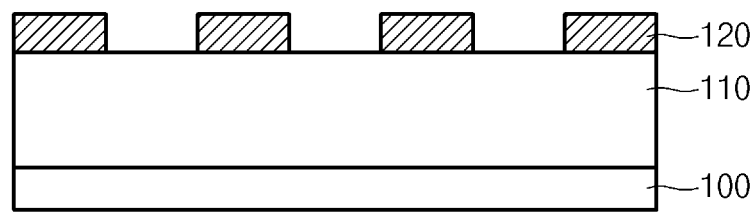
FIGS. 2A to 2C are exemplary cross-sectional views illustrating a method for forming the hydrogen sensor according to an exemplary embodiment of the present invention.
Figure 2B:
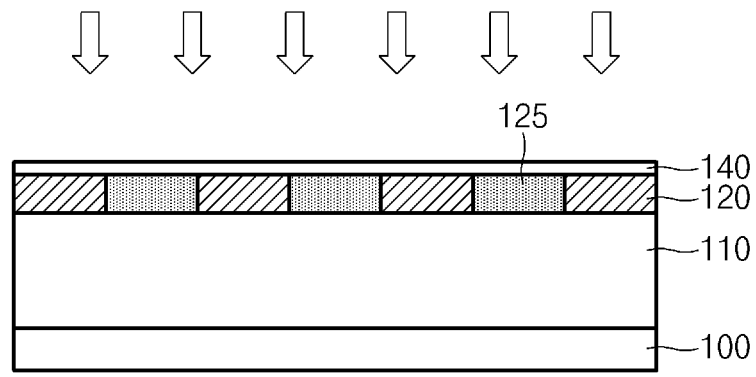
Figure 2C:
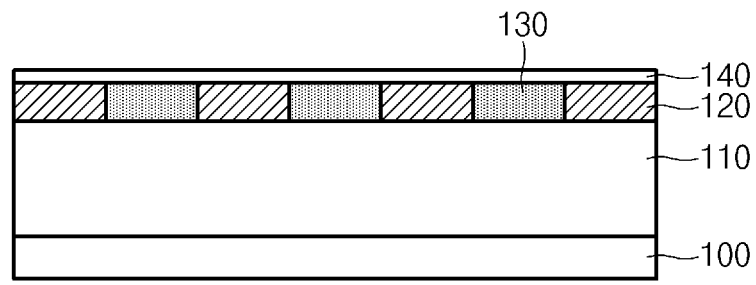

FIGS. 2A to 2C are exemplary cross-sectional views illustrating a method for forming the hydrogen sensor according to an exemplary embodiment of the present invention. A method for forming the hydrogen sensor shown in FIG. 1 will hereinafter be described with reference to FIGS. 2A to 2C. Referring to FIG. 2A, a planarized metal oxide layer 110 may be formed over a substrate 100 and a catalytic layer may be formed over the metal oxide layer 110. The catalytic layer may break hydrogen molecules down into hydrogen atoms, and may be formed of a platinum group metal that reacts to hydrogen. The platinum group metal may be formed of at least one selected from the group consisting of: palladium (Pd), iridium (Ir), ruthenium (Ru), platinum (Pt), rhodium (Rh), gold (Au), and silver (Ag).

Subsequently, several mask patterns, spaced apart from each other by a predetermined distance, may be formed over the catalytic layer. Thereafter, the catalytic layer may be etched using the mask patterns as an etch mask and several catalytic patterns 120 may be formed and the mask patterns may be removed. When the patterned catalytic layer is formed, hydrogen atoms decomposed by the catalytic layer may be rapidly diffused into the metal oxide layer at a higher rate. In addition, physical property variation and discoloration caused by a reaction between the metal oxide layer and the hydrogen atoms may not be interrupted by the catalytic pattern 120, to maintain discoloration reflexibility of the metal oxide layer.

Referring to FIG. 2B, a photoresistant film 125 may be formed over the substrate 100 between the catalytic patterns 120, which may be formed using a spin coating method. A protective layer 140 may be formed over the catalytic pattern 120 and the photoresistant film 125. Ultraviolet (UV) processing may be applied onto the entire upper surface that includes the protective layer 140.

Referring to FIG. 2C, when the photoresist film 125 is removed by UV processing, first recesses 130 may be formed among the catalytic patterns 120. When the photoresistant film 125 is exposed to ultraviolet rays, the photoresistant film 125 may be removed. The received hydrogen molecules or hydrogen atoms may remain within the first recesses 130, which results in an increase in activity contribution of the catalytic pattern 120 that causes the reaction between the metal oxide layer and the hydrogen atoms.

Figure 3:
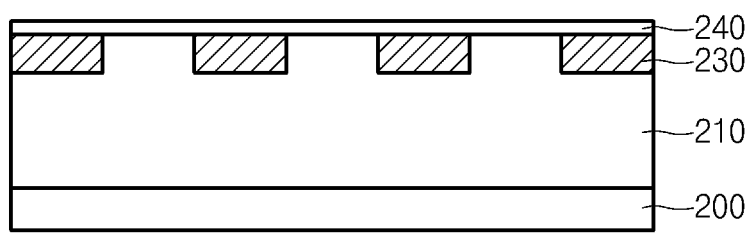
FIG. 3 is an exemplary cross-sectional view illustrating a hydrogen sensor according to an exemplary embodiment of the present invention.

FIG. 3 is an exemplary cross-sectional view illustrating a hydrogen sensor according to an exemplary embodiment of the present invention. Referring to FIG. 3, a metal oxide layer 210 that includes one or more recesses may be formed over the substrate 200. A catalytic pattern 230 disposed within each recess may be formed. The catalytic pattern 230 may break hydrogen molecules down into hydrogen atoms, and may be formed of a platinum group metal that reacts to hydrogen. The platinum group metal may be formed of at least one selected from the group consisting of: palladium (Pd), iridium (Ir), ruthenium (Ru), platinum (Pt), rhodium (Rh), gold (Au), and silver (Ag). A protective layer 240 may be formed over the metal oxide layer 210 and the catalytic pattern 230.

Figure 4A:
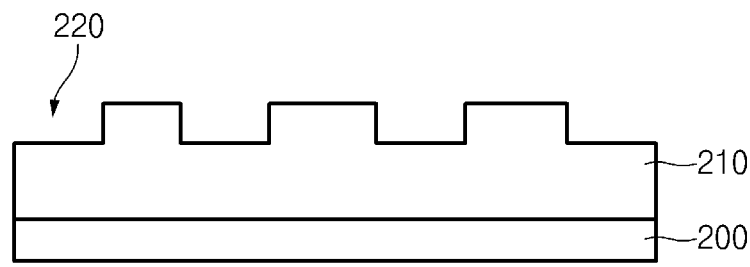
FIGS. 4A to 4C are exemplary cross-sectional views illustrating a method for forming the hydrogen sensor according to an exemplary embodiment of the present invention.
Figure 4B:
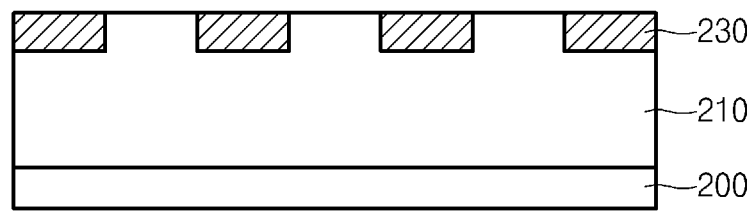
Figure 4C:
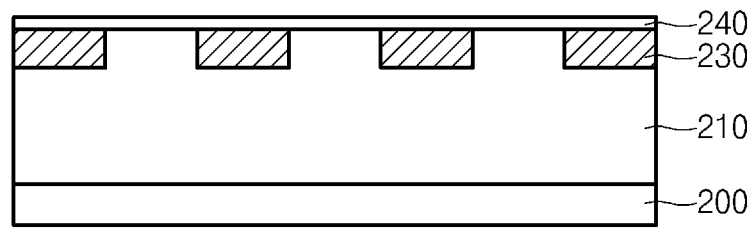

FIGS. 4A to 4C are exemplary cross-sectional views illustrating a method for forming the hydrogen sensor according to an exemplary embodiment of the present invention. A method for forming the hydrogen sensor shown in FIG. 3 will hereinafter be described with reference to FIGS. 4A to 4C.

Referring to FIG. 4A, a metal oxide layer 210 may be formed over (e.g., on top of) a substrate 200. Several mask patterns (not shown), spaced apart from each other by a predetermined distance, may be formed over the metal oxide layer 210. The metal oxide layer 210 may be etched to a predetermined depth using the mask patterns as an etch mask, which results in a plurality of second recesses 220. Concave-convex parts (e.g., uneven parts) may be formed over the metal oxide layer 210 due to the formation of the second recesses 220. Referring to FIG. 4B, a catalytic layer may be formed over the upper surface of the metal oxide layer 210 that includes the second recesses 220. In addition, a Chemical Mechanical Polishing (CMP) process may be applied to dispose a catalytic pattern 230 within each second recess 220. Referring to FIG. 4C, a protective layer 240 may be formed over the metal oxide layer 210 and the catalytic pattern 230.

Figure 5:
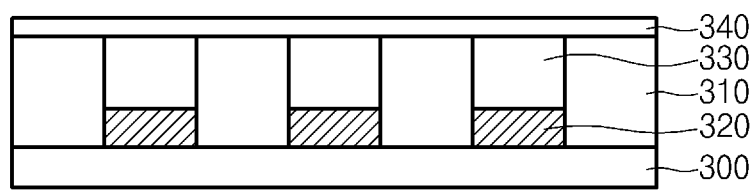
FIG. 5 is an exemplary cross-sectional view illustrating a hydrogen sensor according to an exemplary embodiment of the present invention.

FIG. 5 is an exemplary cross-sectional view illustrating a hydrogen sensor according to an exemplary embodiment of the present invention. Referring to FIG. 5, a plurality of metal oxide patterns 310 may be formed over a substrate 300. A stacked structure of the catalytic pattern 320 and third recesses 330 may be disposed between the metal oxide patterns 310. In particular, the catalytic pattern 320 may break hydrogen molecules down into hydrogen atoms, and may be formed of a platinum group metal that reacts to hydrogen. The platinum group metal may include at least one selected from the group consisting of: palladium (Pd), iridium (Ir), ruthenium (Ru), platinum (Pt), rhodium (Rh), gold (Au), and silver (Ag).

In addition, the received hydrogen molecules or hydrogen atoms may remain within the third recess 330, which increases activity contribution of the catalytic pattern 320 that causes the reaction between the metal oxide layer and the hydrogen atoms. A protective layer 340 may be formed over the metal oxide pattern 310 and the third recesses 330.

Figure 6A:
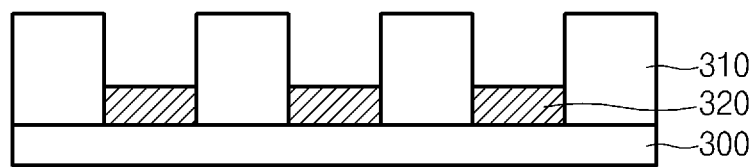
FIGS. 6A to 6C are exemplary cross-sectional views illustrating a method for forming the hydrogen sensor according to an exemplary embodiment of the present invention.
Figure 6B:
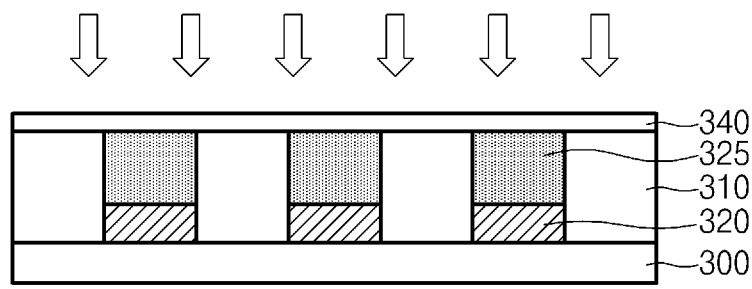
Figure 6C:
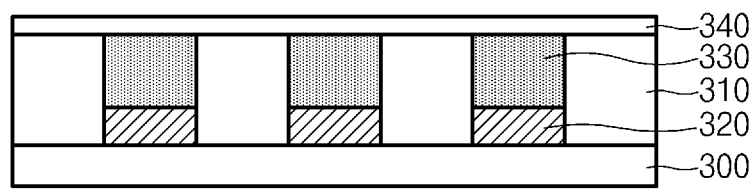

FIGS. 6A to 6C are exemplary cross-sectional views illustrating a method for forming the hydrogen sensor according to an exemplary embodiment of the present invention. A method for forming the hydrogen sensor shown in FIG. 5 will hereinafter be described with reference to FIGS. 6A to 6C.

Referring to FIG. 6A, a metal oxide layer may be formed over a substrate 300. Several mask patterns (not shown), spaced apart from each other by a predetermined distance, may be formed over the metal oxide layer. Thereafter, the metal oxide layer may be etched to a predetermined depth using the mask patterns as an etch mask, which results in the formation of a plurality of metal oxide patterns 310. In particular, the metal oxide layer may be etched until the substrate 300 between the metal oxide patterns 310 is exposed.

A catalytic layer may be formed over the substrate 300 between the metal oxide patterns 310. Thereafter, the catalytic layer between the metal oxide patterns 310 may be further etched to form a catalytic pattern 320 that has a lower height (e.g., shorter) than the metal oxide pattern 310. In other words, a step difference may occur between the metal oxide pattern 310 and the catalytic pattern 320. The catalytic pattern 320 that has a thickness of at least about 3 nm may remain unetched.

Referring to FIG. 6B, spin coating may be processed within the recess formed by a step difference between the metal oxide pattern 310 and the catalytic pattern 320, to dispose a photoresistant material 325 within the empty space. The protective layer 340 may be formed over the metal oxide pattern 310 and the photoresistant material 325. Ultraviolet (UV) processing may be applied to the entire upper surface that includes the protective layer 340. Referring to FIG. 6C, when the photoresistant material 325 is exposed to ultraviolet (UV) rays, the photoresistant material 325 may be removed by UV processing. As a result, the third recesses 330 may be formed over the catalytic patterns 320.

Figure 7:
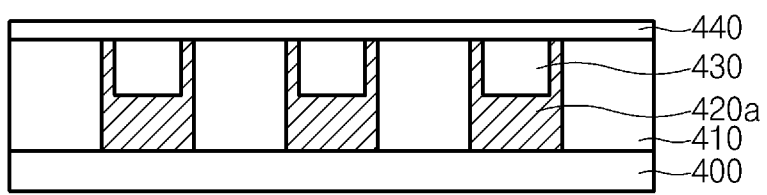
FIG. 7 is an exemplary cross-sectional view illustrating a hydrogen sensor according to an exemplary embodiment of the present invention.

FIG. 7 is an exemplary cross-sectional view illustrating a hydrogen sensor according to an exemplary embodiment of the present invention. Referring to FIG. 7, a plurality of metal oxide patterns 410 may be formed over a substrate 400. Substantially U-shaped catalytic patterns 420 may be formed within the metal oxide patterns 410, and fourth recesses 430 may be formed over the catalytic patterns 420. A protective layer 440 may be formed over the metal oxide pattern 410, the catalytic pattern 420, and fourth recesses 430.

Figure 8A:
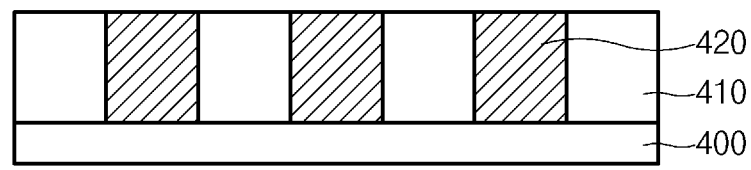
FIGS. 8A to 8D are exemplary cross-sectional views illustrating a method for forming the hydrogen sensor according to an exemplary embodiment of the present invention.

FIGS. 8A to 8D are exemplary cross-sectional views illustrating a method for forming the hydrogen sensor according to an exemplary embodiment of the present invention. A method for forming the hydrogen sensor shown in FIG. 7 will hereinafter be described with reference to FIGS. 8A to 8D. Referring to FIG. 8A, a metal oxide layer may be formed over the substrate 400. Several first mask patterns (not shown), spaced apart from each other by a predetermined distance, may be formed over the metal oxide layer. A plurality of metal oxide patterns 410 may be formed by etching the metal oxide layer using the first mask patterns as an etch mask. In particular, the metal oxide layer may be continuously etched until the substrate 400 is exposed.

Figure 8B:
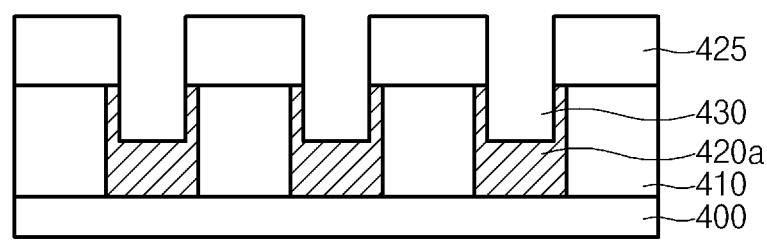

A catalytic layer 420 may be formed over the substrate 400 between the metal oxide patterns 410. Subsequently, a second mask pattern 425 may be formed between the metal oxide patterns 410 to open the catalytic layer 420. In particular, the second mask pattern 425 may have a greater critical dimension (CD) than the metal oxide pattern 410, and some parts of the center part of the catalytic layer 420 may be exposed. Referring to FIG. 8B, the catalytic layer 420 may be etched using the second mask pattern 425 as an etch mask, which results in formation of the catalytic pattern 420a. The catalytic pattern 420a may be formed in a substantially U-shape along a sidewall of the metal oxide pattern 410 and an upper portion of the substrate 400, such that a recess is formed at an upper portion of the catalytic pattern 420a. When the U-shaped catalytic pattern 420a is formed, the surface area of the catalytic pattern 420a exposed to hydrogen may be substantially increased.

Figure 8C:
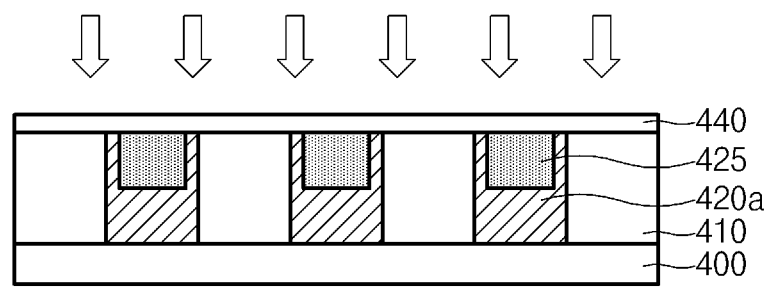
Figure 8D:
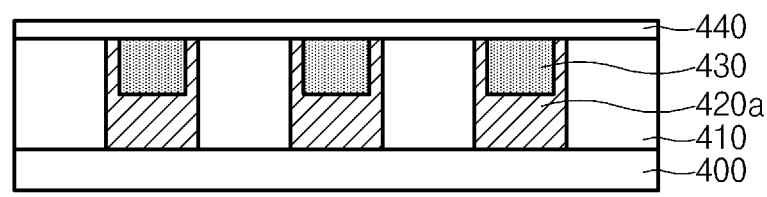

Referring to FIG. 8C, spin coating may be processed within the recess disposed at an upper portion of the catalytic pattern 420a, to dispose a photoresistant material 425 within a recess. A protective layer 440 may be formed over the metal oxide pattern 410 and the photoresistant material 425. Ultraviolet (UV) processing may then be applied to the entire (e.g., whole) upper surface that includes the protective layer 440. Referring to FIG. 8D, when the photoresistant material 425 is exposed to ultraviolet (UV) rays, the photoresistant material 425 may be removed to form a recess 430 at an upper portion of each catalytic pattern 420.

Figure 9:
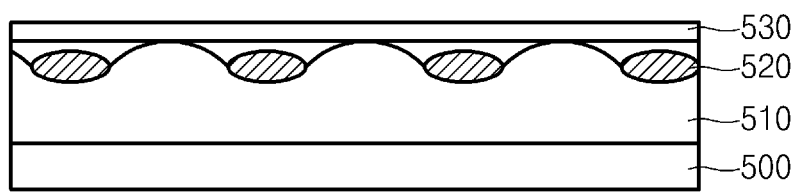
FIG. 9 is an exemplary cross-sectional view illustrating a hydrogen sensor according to an exemplary embodiment of the present invention.

FIG. 9 is an exemplary cross-sectional view illustrating a hydrogen sensor according to an exemplary embodiment of the present invention. Referring to FIG. 9, a metal oxide layer 510 that has an embossed surface may be formed over a substrate 500. A catalytic pattern 520 may be formed within a recessed part of the metal oxide layer 510. In addition, a protective layer 530 may be formed over the catalytic pattern 520 and the metal oxide layer 510. When the metal oxide layer 510 is formed by the embossing process, the metal oxide layer 510 that reacts to hydrogen atoms may increase in size.

FIGS. 10A to 10C are exemplary cross-sectional views illustrating a method for forming the hydrogen sensor according to an exemplary embodiment of the present invention. A method for forming the hydrogen sensor shown in FIG. 9 will hereinafter be described with reference to FIGS. 10A to 10C.

Referring to FIG. 10A, a metal oxide layer 510 may be formed over the substrate 500. In particular, an upper portion of the metal oxide layer 510 may be embossed. FIG. 10B-(ii) is an exemplary enlarged view illustrating the embossed metal oxide layer 510. Plate-type two-dimensional (2D) nano structures may be mixed in a substantially complicated manner as shown in FIG. 10B(ii), such that the resultant 2D nano structures may be formed in a substantially embossed shape. The above-mentioned structure may be synthesized by a hydrothermal synthesis method.

Referring to FIG. 10B, a catalytic pattern 520 may be formed within a recessed part that indicates a minimal step difference between the embossed metal oxide layer 510. However, the scope or spirit of the catalytic pattern 520 of the present invention is not limited thereto. When the metal oxide layer 510 is formed as a two-dimensional nano structure and the catalytic layer is formed over the entire surface, the catalytic pattern 520 may be formed within the recesses between the nano structures. Referring to FIG. 10C, a protective layer 530 may be formed over the metal oxide layer 510 over which the catalytic pattern 520 may be formed. In particular, some recesses may be disposed between the embossed metal oxide layers 510.

As is apparent from the above description, the exemplary embodiments of the present invention have the following effects. First, hydrogen molecules may be broken down into hydrogen atoms within the catalytic layer. In addition, the hydrogen atoms may not move toward the metal oxide layer after passing through a catalytic layer and a reaction may occur within a metal oxide material adjacent to the catalytic layer. Thus, diffusion speed of hydrogen atoms may be prevented from decreasing.

Second, related art, in which a catalytic layer is deposited over the surface, may have a catalytic layer that decrease discoloration reflexibility of the metal oxide material, to optimize thickness of the conventional catalytic layer to prevent reduction of discoloration reflexibility. However, the optimization process has a substantially high level of difficulty in fabrication. In contrast, according to exemplary embodiments of the present invention, a patterned catalytic layer may be formed, and physical property variation and discoloration caused by reaction between the hydrogen atom and the metal oxide material may not be interrupted by the catalytic layer. Further, the discoloration reflexibility of the metal oxide material may be maintained.

Third, according to the hydrogen sensor of the related art, hydrogen must disappear after passing through the catalytic layer, when discoloration due to a lack of hydrogen arises. In particular, a predetermined time may be used for hydrogen diffusion, so that a response delay is required. In contrast, according to the exemplary embodiments of the present invention, a patterned catalytic layer may be applied to a reversible sensor that is capable of repeatedly performing coloration and discoloration. The reversible sensor may be configured to detect physical variation when exposed to hydrogen. When the hydrogen is not present, the reversible sensor may return to an initial value. Accordingly, the reversible sensor may be configured to repeatedly detect hydrogen leak.

Fourth, the hydrogen sensor may be configured to detect a physical variation, when the hydrogen sensor is exposed to hydrogen. When the hydrogen is not present, the hydrogen sensor may return to an initial value. In other words, the hydrogen sensor may be configured to repeatedly detect a hydrogen leak.

Although the exemplary embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A hydrogen sensor, comprising:
   a substrate;
   a metal oxide layer formed over the substrate;
   a catalytic pattern formed over the metal oxide layer;
   a protective layer formed over the metal oxide layer and the catalytic pattern;
   a second recess formed over an upper surface of the metal oxide layer; and
   wherein the catalytic pattern is disposed within the second recess.

2. The hydrogen sensor according to claim 1, further comprising:
   at least one first recess formed at an upper portion of the metal oxide layer among the catalytic patterns.

3. The hydrogen sensor according to claim 1, wherein a top surface of the metal oxide layer is formed in a substantially embossed shape.

4. The hydrogen sensor according to claim 3, wherein the catalytic pattern is disposed at a lower portion among the substantially embossed metal oxide layers.

5. The hydrogen sensor according to claim 1, wherein:
   the metal oxide layer includes one selected from the group consisting of: vanadium, niobium, tantalum, chromium, molybdenum, and tungsten, and
   the catalytic pattern includes at least one selected from the group consisting of: palladium, iridium, ruthenium, platinum, rhodium, gold, and silver.

* * * * *